United States Patent [19]

Kaufhold, Jr. et al.

[11] Patent Number: 5,000,736
[45] Date of Patent: Mar. 19, 1991

[54] DISPOSABLE SYRINGE WITH AUTOMATIC NEEDLE RETRACTION

[75] Inventors: Harry Kaufhold, Jr., 9711 Ebb St., Houston, Tex. 77089; Martin Jasso, Houston; Gerald E. Kruckeberg, Cypress, both of Tex.

[73] Assignee: Harry Kaufhold, Jr., Houston, Tex.

[21] Appl. No.: 497,458

[22] Filed: Mar. 22, 1990

[51] Int. Cl.⁵ ............................................. A61M 5/00
[52] U.S. Cl. .................................... 604/110; 604/195
[58] Field of Search ............... 604/110, 195, 187, 192, 604/218, 210, 263, 198

[56] References Cited

U.S. PATENT DOCUMENTS

| | | | |
|---|---|---|---|
| 3,008,570 | 11/1961 | Roehr et al. | 206/43 |
| 3,107,785 | 10/1963 | Roehr et al. | 206/63.2 |
| 3,895,633 | 7/1975 | Bartner et al. | 128/218 |
| 3,976,069 | 8/1976 | Ong | 128/218 |
| 4,300,678 | 11/1981 | Gyure et al. | 206/364 |
| 4,356,822 | 11/1982 | Winstead-Hall | 128/215 |
| 4,425,120 | 1/1984 | Sampson et al. | 604/198 |
| 4,592,744 | 6/1986 | Jagger et al. | 604/192 |
| 4,639,249 | 1/1987 | Larson | 604/198 |
| 4,643,200 | 2/1987 | Jennings, Jr. | 128/763 |
| 4,655,751 | 4/1987 | Harbaugh | 604/198 |
| 4,666,435 | 5/1987 | Braginetz | 604/198 |
| 4,675,005 | 6/1987 | DeLuccia | 604/110 |
| 4,692,156 | 9/1987 | Haller | 604/195 |
| 4,723,943 | 2/1988 | Spencer | 604/198 |
| 4,738,663 | 4/1988 | Bogan | 604/198 |
| 4,747,830 | 5/1988 | Gloyer et al. | 604/110 |
| 4,790,822 | 12/1988 | Haining | 604/110 |
| 4,816,022 | 3/1989 | Poncy | 604/198 |
| 4,826,483 | 5/1989 | Molnar, IV | 604/110 |
| 4,840,619 | 6/1989 | Hughes | 604/187 |
| 4,950,241 | 8/1990 | Ranford | 604/110 |
| 4,950,251 | 8/1990 | Haining | 604/195 X |

Primary Examiner—John D. Yasko
Attorney, Agent, or Firm—William E. Shull; David A. Rose

[57] ABSTRACT

A medicinal syringe including a tubular plunger from which air has been evacuated and a seal member releasably attached on the distal end of the plunger. Upon application of a predetermined longitudinal axial force to the seal member, the attachment between the seal member and the plunger will rupture, releasing the seal member for movement within the plunger. The seal member when released will be forced by the differential pressure between the vacuum and the ambient air into the interior of the tubular plunger. The plunger is slidably disposed in a tubular barrel. A needle is disposed in a hub releasably attached within the distal end of the barrel. Upon application of a predetermined longitudinal axial force to the hub, the attachment between the hub and the barrel will rupture, releasing the hub for movement within the barrel. The hub when released will be forced by the pressure differential, along with the distal plunger seal member, into the interior of the tubular plunger, carrying the needle with it. The attachment between the hub and barrel is adapted to rupture prior to that between the seal member and plunger. Once drawn into the tubular plunger, the needle and hub will remain there indefinitely, thus eliminating accidental puncturing by the needle of a person in the vicinity of the syringe.

8 Claims, 4 Drawing Sheets

DISPOSABLE SYRINGE WITH AUTOMATIC NEEDLE RETRACTION

BACKGROUND OF THE INVENTION

The present invention relates generally to medical instruments, and more particularly to a safety-disposable medicinal syringe. Still more particularly, the present invention relates to a disposable syringe having a releasable needle hub which, when released, is actuated by ambient air pressure into retraction into an evacuated plunger, carrying the needle with it.

A problem for doctors, nurses, and other health care personnel who use or handle medicinal syringes is accidental puncture of the skin by the needle. The problem can be very serious if the needle has been used. Potentially fatal diseases, such as hepatitis or Acquired Immune Deficiency Syndrome (AIDS), can be contracted if the needle has been used on an infected subject.

The syringe needle is typically covered with a removable sheath prior to and following use to prevent accidental contact, but the act of replacing the sheath after use can still result in accidental skin puncture. Also, if the sheath is not securely repositioned, the danger exists that personnel subsequently involved in disposal of the device may become infected by accidental puncture.

Solutions that attempt to better protect the health care worker include that disclosed in U.S. Pat. No. 4,790,822. The 822 patent discloses a disposable syringe in which the needle can be first captured by the plunger and then withdrawn into the barrel in a position with the needle completely protected by the barrel. The plunger can then be broken off, leaving the broken end flush with the end of the barrel, so that the needle cannot be accidentally pushed out from the barrel and exposed.

U.S. Pat. No. 4,747,830 discloses a similar system, with a plunger that can be broken off once the needle is retracted into the barrel. U.S. Pat. Nos. 4,692,156 and 4,675,005 both disclose disposable syringes wherein the needle can be retracted into the barrel. U.S. Pat. No. 4,643,200 discloses a similar system, used with a blood donor assembly, which allows retraction of a needle into a barrel.

U.S. Pat. No. 4,425,120 discloses a needle guard movable on the syringe barrel between an extended position in which the needle guard shields the needle and a retracted position in which the needle is exposed for use. U.S. Pat. No. 4,816,022 discloses a syringe with a sliding cap for preventing accidental puncture. The 022 patent utilizes a nub and backseat for engagement of a nosepiece for securing the cap around the syringe for safety purposes. U.S. Pat. No. 3,008,570 discloses use of a removable cap for the purpose of enclosing and protecting a sterilized syringe in a transport. U.S. Pat. No. 4,840,619 discloses a syringe assembly that has a transport held in telescoping position over a syringe by flanges. Other and various means of sheathing or shielding a syringe are shown in the following U.S. Pat. Nos. 4,738,663; 4,723,943; 4,666,435; 4,655,751; 4,639,249; 4,592,744; 4,356,822; 4,300,678; 3,976,069; 3,895,633; 3,107,785. U.S. Pat. No. 4,826,483 discloses a non-reusable syringe with a one-way movable piston.

The present invention improves upon these devices by providing a means of automatically, without the need of unusual manipulation, rendering a used syringe safe for handling immediately after use and throughout subsequent disposal procedures, as well as rendering it unsuitable for further use.

SUMMARY OF THE INVENTION

The present invention comprises a medicinal syringe including a tubular plunger from which air has been evacuated and a seal member releasably attached on the distal end of the plunger. Upon application of a predetermined longitudinal axial force to the seal member, the attachment between the seal member and plunger will break, releasing the seal member for movement within the plunger. The seal member when released will be forced by the differential pressure between the vacuum and the ambient air into the interior of the tubular plunger. The plunger is slidably disposed in a tubular barrel. A needle is disposed in a hub releasably attached within the distal end of the barrel. Upon application of a predetermined longitudinal axial force to the hub, the attachment between the hub and the barrel will break, releasing the hub for movement within the barrel. The hub when released will be forced by the pressure differential, along with the distal plunger seal member, into the interior of the tubular plunger, carrying the needle with it. The attachment between the hub and barrel is adapted to rupture prior to that between the seal member and plunger. Once forced into the tubular plunger, the needle and hub will remain there indefinitely, thus eliminating accidental puncturing by the needle of a person in the vicinity of the syringe.

The present invention thus comprises a container having a nozzle or needle at its distal end and a central cavity, the volume of which is determined by the position of a proximally disposed plunger. The nozzle or needle is mounted in the container such that application of a predetermined longitudinal axial force to the nozzle or needle will cause its detachment from the container. The plunger contains a hollow and evacuated center, sealed at its distal end by a member that is designed to break free from the plunger upon application of a predetermined longitudinal axial force to the member. This distal member may also serve to provide a leak free seal between the central cavity of the container and the atmosphere.

In its preferred embodiment, the invention is used in accordance with standard procedures for the subcutaneous, intramuscular, of intravascular injection or aspiration of substances into or out of the body, which procedures are well known to those schooled in the art. Immediately following the procedure, longitudinal axial force is applied to the proximal end of the plunger, thereby detaching the needle from the container and rupturing the vacuum seal at the distal end of the plunger. Atmospheric pressure then forces the needle up into the evacuated center of the plunger and holds it there, rendering it incapable of puncturing the skin of the primary user or of personnel involved in secondary handling of the device.

The invention will now be described in further detail with reference to the accompanying drawings.

DETAILED DESCRIPTION OF THE PREFERRED EMBODIMENTS

Figure 1:
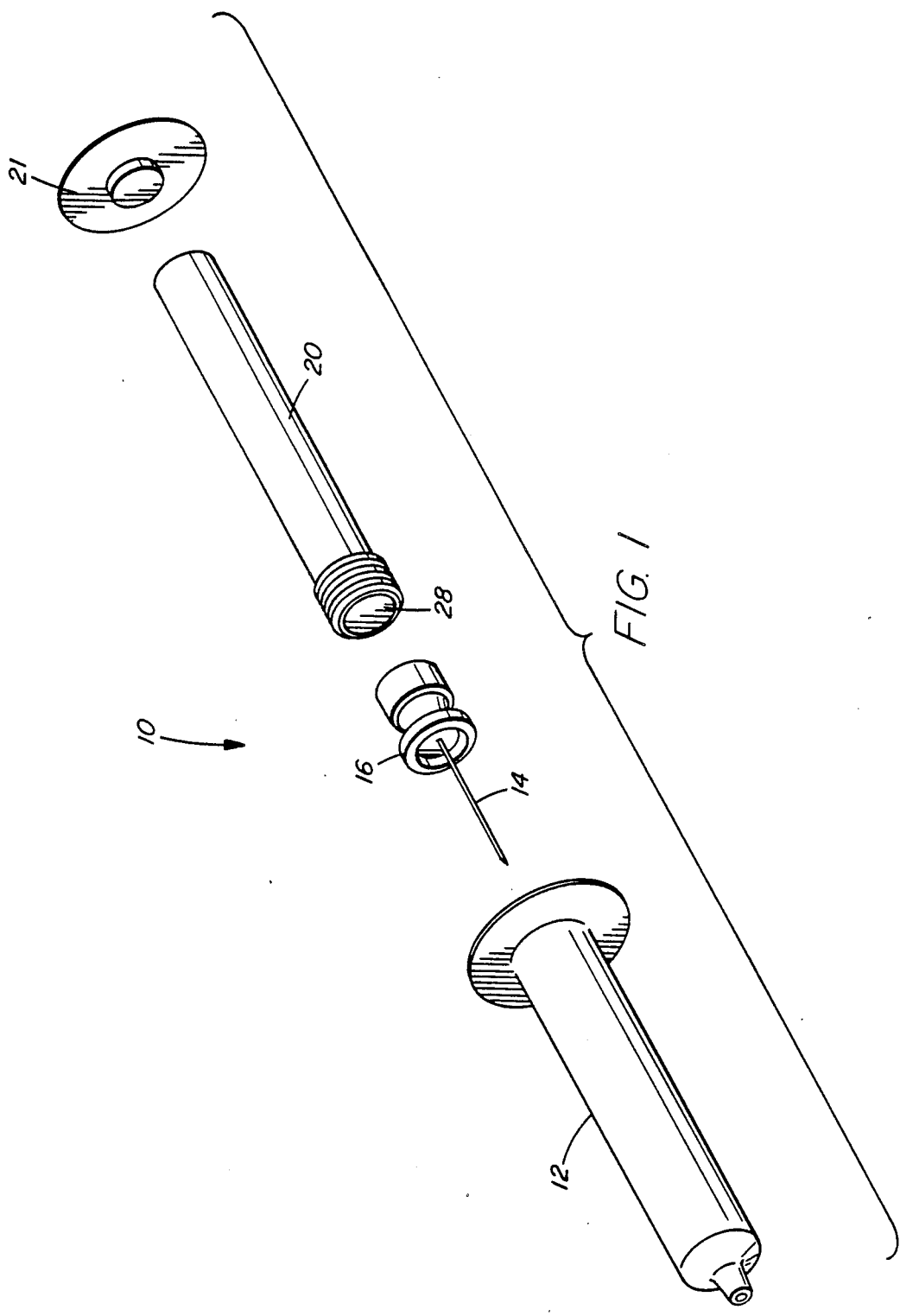
FIG. 1 is an exploded pictorial view of a syringe of a preferred embodiment of the invention.

While the invention is satisfied in many different forms, there is shown in the drawings and will herein be described in detail preferred embodiments of the invention, with the understanding that the present disclosure is to be considered as exemplary of the principles of the invention and is not intended to limit the scope of the invention to the embodiments illustrated.

Figure 2:
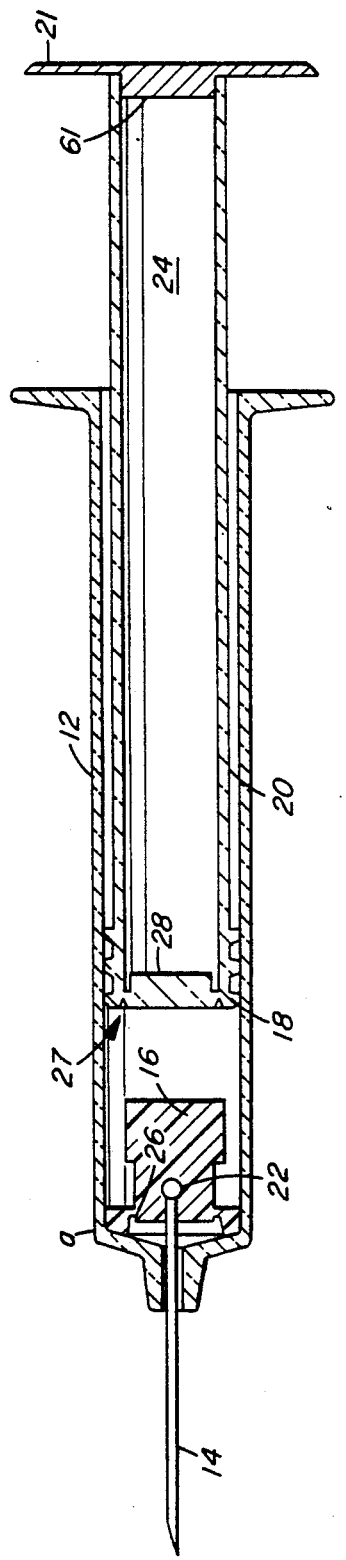
FIG. 2 is a vertical cross-sectional view of the syringe of FIG. 1 prior to use.
Figure 3:
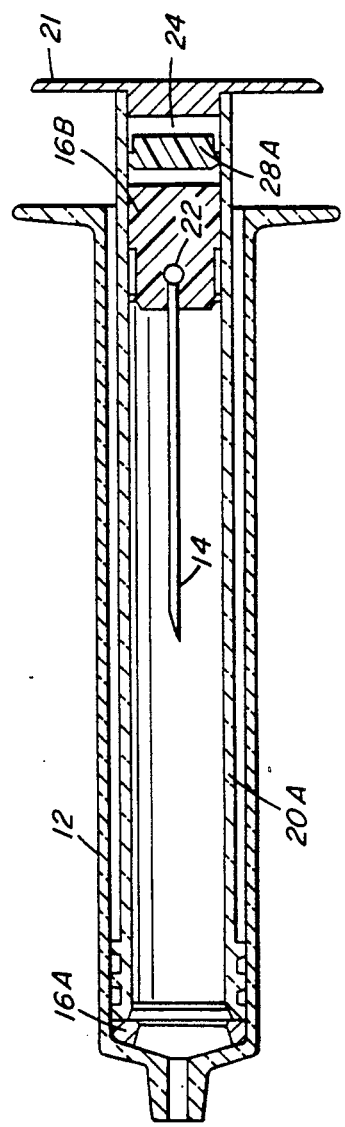
FIG. 3 is a vertical cross-sectional view of the syringe of FIG. 1 following use and actuation of the automatically retractable needle of the invention.

The embodiment shown as syringe assembly 10 in FIGS. 1-3 includes a hypodermic needle 14 that is inserted and mounted into a needle hub 16 in such a manner that the interior bore of the needle communicates with the exterior of the hub via a transversely extending hole 22 in the hub. Hub 16 is releasably attached to the interior of syringe barrel 12 in such a manner that it forms a circumferential seal around the inner periphery of the barrel at its distal end a. Barrel 12 and hub 16 may be made of plastic, glass, or other materials suitable to the intended use of the device.

Slidably disposed within the barrel 12 is a hollow plunger tube 20 made of plastic, glass, or the like, which is sealed at its distal and proximal ends by a barrier seal member 28 and a cap 21, respectively. Cap 21 may be, for example, a thin round disc-like member having a circular boss 61 protruding therefrom and receivable within the interior of plunger 20. Alternatively, the cap may have a circular wall extending from the disc surface and adapted for receiving the exterior of the plunger therewithin. Other means of mounting a cap on the proximal end of plunger 20 will no doubt be readily apparent to those skilled in the art. During or after the process of sealing cap 21 to plunger tube 20, the air is removed from the sealed interior of the plunger, leaving a vacuum 24 within the plunger tube 20. Cap 21 may be made of plastic, rubber, glass, metal or the like.

In FIG. 2 it can be seen that hub 16 and barrier seal member 28 are constructed so as to comprise annular grooves 26 and 27, respectively, forming relatively thin-walled areas of hub 16 and barrier seal member 27. Grooves 26, 27 may be on the distal, proximal, or both faces of hub 16 and barrier seal member 28, and are so designed that the thin-walled portions of these elements so created will rupture relatively easily upon the application of longitudinal axial force on the elements that is greater than that force required to reciprocate plunger 20 in barrel 28 to dispense fluids from or draw fluids into barrel 28 to achieve normal, pre-disposal syringe functions. Hub 16 and barrier seal member 28 may be subsequent attachments to or an integral part of their respective supporting members, barrel 12 and plunger 20.

At the election of the operator, normally after completion of a specific procedure, the plunger 20 is pushed distally into the barrel 12 with enough force to rupture the thin-walled areas of hub 16 and seal member at grooves 26 and 27. The needle hub center 16B, along with the central disc portion 28A of the barrier seal member 28, will be forced by the differential pressure between the atmosphere and the vacuum 24 up into the interior of vacuum tube 20A. The hub center portion 16B and the central disc portion 28A are sized so that they will closely engage the interior wall of the plunger 20 and will be retained in their retracted positions by friction. The hub center portion 16B and the central disc portion 28A may also be sized, and made of a sufficiently resilient material, to sealingly engage the interior wall of the plunger 20 in their retracted positions, in which case they will also be retained inside plunger 20 by the difference in pressure between the atmosphere and the interior of the relatively evacuated area 24. With the hub portion 16B, and hence the needle 14, retracted within plunger 20, the syringe assembly 10 may be safely disposed of without fear of accidental puncture.

Figure 4:
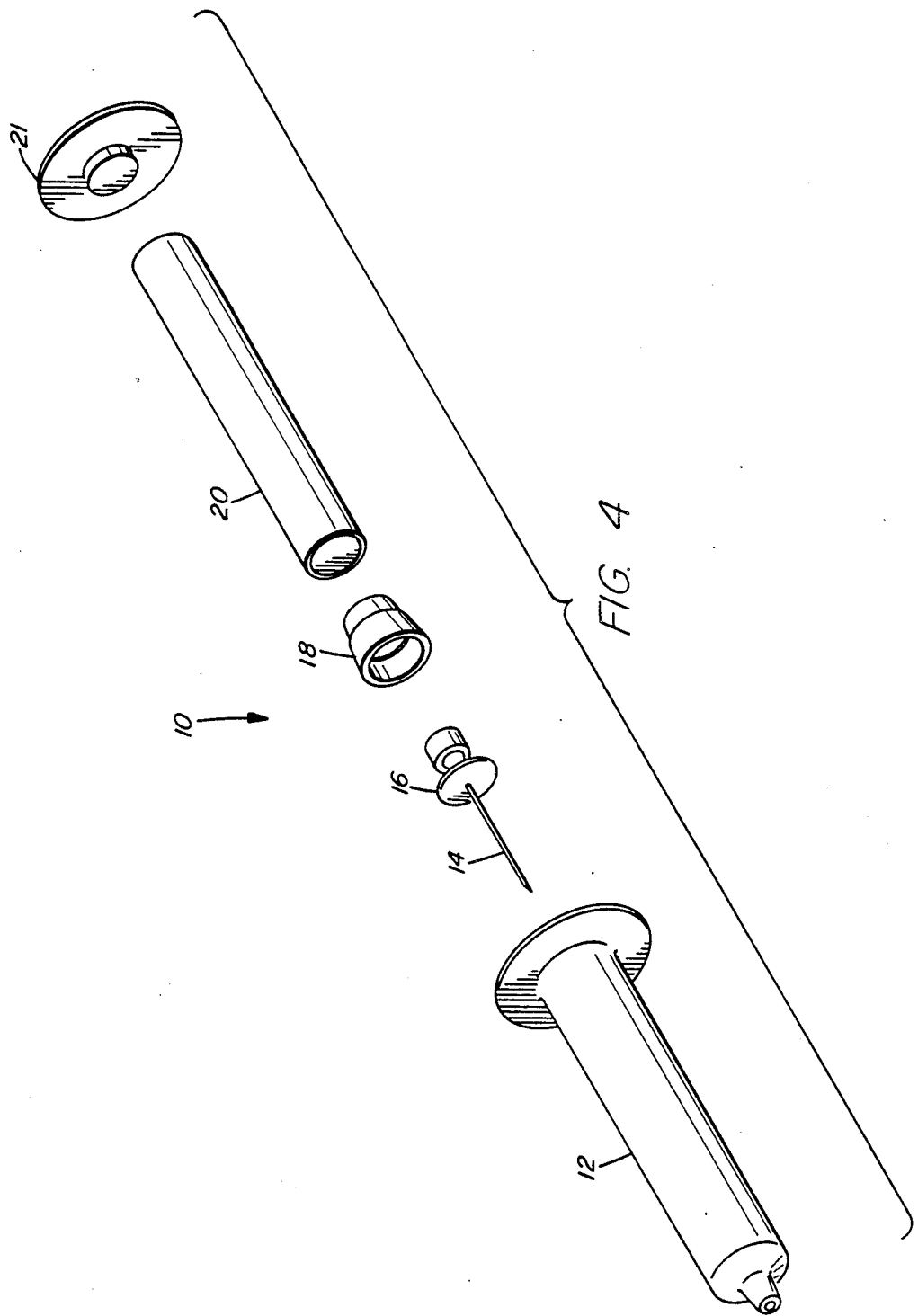
FIG. 4 is an exploded pictorial view of a syringe of a second embodiment of the invention.
Figure 5:
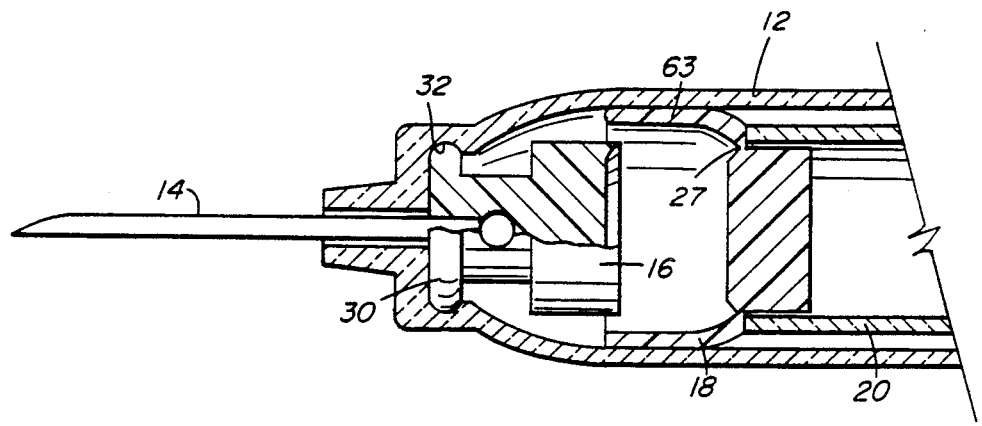
FIG. 5 is a vertical cross-sectional view of the distal end of the second embodiment showing an alternate construction.

FIGS. 4 and 5 show an alternate construction of syringe assembly 10, in which hub 16 is constructed with an annular shoulder 30 around its distal end which seats in and forms a seal against a correlatively shaped annular groove 32 around the inner periphery of the distal end of barrel 12. End seal member 18 is mounted on the distal end of plunger 20. End seal member 18 has a distally extending skirt portion 63 therearound, designed so that its longitudinal distal advancement in barrel 12 will spread apart the inner walls of barrel 12 and open groove 32, thereby releasing needle 14 and hub 16 to be drawn into plunger tube 20 when annular thin-walled ring portion 27 on end seal member 18 is ruptured.

Figure 6:
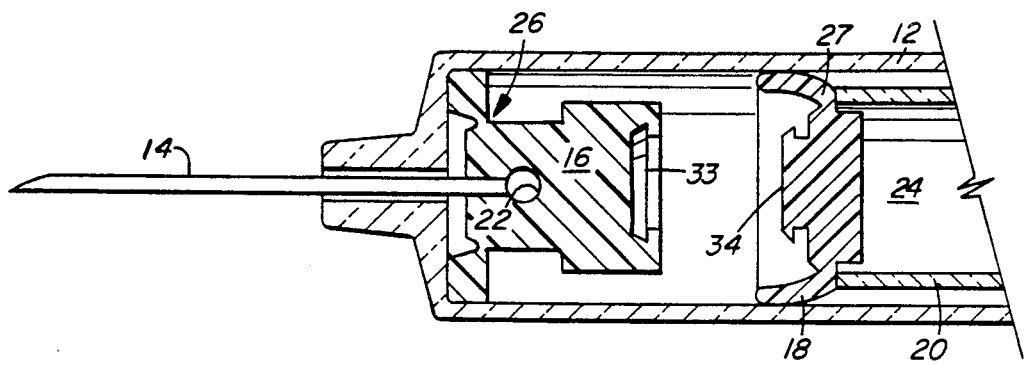
FIG. 6 is a vertical cross-section of the distal end of the preferred embodiment showing an alternate locking construction.

FIG. 6 shows an alternate construction in which hub 16 contains a locking recess 33 in its proximal end. The distal end face of end seal member 18 has centrally disposed thereon a projection or locking hub 34 which is shaped correlatively to recess 33. Recess 33 and hub 34, which may have any of a variety of configurations or profiles, are so designed that when plunger 20 is advanced toward hub 16, the hub 16 and end seal member 18 will engage and lock together just prior to the subsequent rupture of grooves 26 and 27, respectively. It should be understood that the recess 33 can be disposed in the end seal member 18, and the locking hub 34 can be disposed on the needle hub 16. As in the preferred construction shown in FIGS. 1-3, the needle 14 and hub 16 are drawn into the vacuum space 24 of plunger tube 20.

Figure 7:
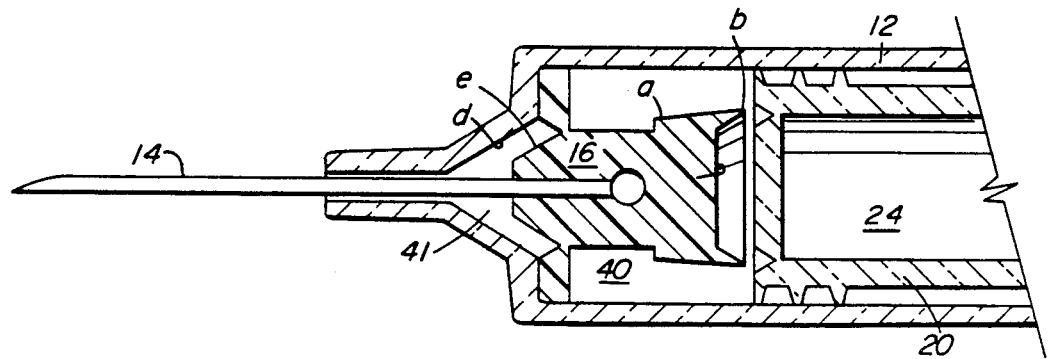
FIG. 7 is a vertical cross-sectional view of the distal end of the preferred embodiment showing an alternate construction.

FIG. 7 shows an alternate construction of the distal portion of the preferred embodiment of the syringe assembly of the present invention. Hub 16 includes a frustoconical-shaped recess or concavity c in its proximal end face, and a frustoconical-shaped or sloped exterior surface extending from location a to location b. Combined, the recess or concavity c, and the sloped surface a-b, form a thin walled, compressible, flexible annular lip which, when drawn into vacuum space 24 of plunger tube 20, will result in an enhanced seal against the interior of plunger tube 20. Hub 16 also includes a frustoconical-shaped surface or taper e at its distal end, and barrel 12 includes a frustoconical-shaped surface or taper d at its distal end. Tapers d and e serve to reduce the resultant volume of the space 40 surrounding hub 16 and integral to barrel 12 when in the pre-use condition as well as to reduce space 41, distal to the hub 16 and open to atmosphere.

Having described certain embodiments of the present invention, many modifications thereof may be made within the scope of the inventive concept taught herein and set out in the following claims. The preferred embodiments described in the foregoing specification are exemplary only, and not limiting. The scope of protection herein sought also includes all equivalents of the subject matter of the claims.

We claim:

1. A disposable syringe assembly, comprising:
    a barrel having a proximal end and a distal end and an internal central bore;
    a tubular plunger having a closed proximal end, said plunger being telescopingly insertable within the proximal end of said barrel and adapted for sliding reciprocating movement therewithin;
    a needle hub sealingly mounted around the inner wall of said barrel, said needle hub having a releasable center portion adapted for movement within said barrel when released, the distal end of said barrel having an opening therein exposing the distal face of said releasable center portion of said needle hub to the atmosphere;
    a needle retained in said releasable center portion of said needle hub and projecting out said opening in said distal end of said barrel prior to release of said center portion of said hub;
    a barrier seal member sealingly mounted on the distal end of said plunger, said barrier seal member having a releasable center portion adapted for movement within said tubular plunger when released, said barrier seal member closing and sealing the distal end of said plunger prior to release of said releasable center portion of said barrier seal member, the interior of said tubular plunger being relatively evacuated;
    said releasable center portions of said hub and said barrier seal member being engageable with one another and releasable upon application of a predetermined longitudinal axial force thereon, the distal face of said releasable center portion of said barrier seal member being exposed to the atmosphere when said releasable center portion of said hub has been released, said releasable center portions of said hub and said barrier seal member being forced when released into the relatively evacuated interior of said plunger by differential pressure between said evacuated interior and the atmosphere.

2. The disposable syringe assembly of claim 1, wherein said predetermined force is imparted by longitudinal distal movement of said plunger within said barrel.

3. The disposable syringe assembly of claim 1, wherein said needle hub includes an annular groove in one of its distal and proximal faces forming a thin-walled hub portion, said releasable center portion of said hub being circumscribed by said thinwalled hub portion.

4. The disposable syringe assembly of claim 1, wherein said barrier seal member includes an annular groove in one of its distal and proximal faces forming a thin-walled barrier seal member portion, said releasable center portion of said barrier seal member being circumscribed by said thin-walled barrier seal member portion.

5. The disposable syringe assembly of claim 3, wherein one of the proximal end of said needle hub and the distal end of said barrier seal member includes a locking recess therein, and the other of the proximal end of said needle hub and the distal end of said barrier seal member includes a locking hub shaped correlatively to said locking recess, said locking hub being lockingly received in said locking recess when said barrier seal member engages said needle hub.

6. The disposable syringe assembly of claim 3, wherein said needle hub includes a frustoconical recess in its proximal end face and the proximal end portion of said needle hub comprises a frustoconical-shaped exterior surface tapering distally, forming a thin-walled annular lip around the proximal end of said needle hub.

7. The disposable syringe assembly of claim 6, wherein the distal end of said releasable center portion of said needle hub comprises a frustoconical-shaped exterior surface tapering distally, and said barrel includes a correlatively shaped frustoconical surface around the distal end of said barrel adjacent to and spaced from said frustoconical-shaped surface on the distal end of said needle hub, prior to release of said releasable center portion of said needle hub.

8. A disposable syringe assembly, comprising:
    a barrel having a proximal end and a tapering distal end and an internal central bore;
    a tubular plunger having a closed proximal end, said plunger being telescopingly insertable within the proximal end of said barrel and adapted for sliding reciprocating movement therewithin;
    a needle hub releasably and sealably mounted around the inner wall of said barrel, said needle hub having an annular shoulder around its distal end, said barrel having an annular groove around its inner periphery for releasably retaining said annular shoulder of said needle hub therewithin, said needle hub being adapted for movement within said barrel when said shoulder is released from said groove, the distal end of said barrel having an opening therein exposing the distal face of said needle hub to the atmosphere;
    a needle retained in said needle hub and projecting out said opening in said distal end of said barrel prior to release of said needle hub from said barrel groove;
    a barrier seal member sealingly mounted on the distal end of said plunger, said barrier seal member having a releasable center portion adapted for movement within said tubular plunger when released, said barrier seal member closing and sealing the distal end of said plunger prior to release of said releasable center portion of said barrier seal member, the interior of said tubular plunger being relatively evacuated;
    said barrier seal member having a distally extending skirt portion engageable with the interior of the tapering distal end of said barrel, spreading the inner wall of said barrel at said groove, when said plunger is advanced distally within said barrel releasing said annular needle hub shoulder from said groove, said releasable center portion of said barrier seal member being releasable upon application of a predetermined longitudinal axial force thereon, the distal face of said releasable center portion of said barrier seal member being exposed to the atmosphere when said needle hub has been released, said needle hub and said releasable center of said barrier seal member being forced when released into the relatively evacuated interior of said plunger by differential pressure between said evacuated interior and the atmosphere.

* * * * *